(12) United States Patent
Buescher et al.

(10) Patent No.: US 9,969,976 B2
(45) Date of Patent: May 15, 2018

(54) CELL POPULATIONS HAVING IMMUNOREGULATORY ACTIVITY, METHODS FOR THE PREPARATION AND USES THEREOF

(75) Inventors: Dirk Buescher, Madrid (ES); Olga De La Rosa, Madrid (ES)

(73) Assignee: CELLERIX, S.A., Madrid (ES)

( * ) Notice: Subject to any disclaimer, the term of this patent is extended or adjusted under 35 U.S.C. 154(b) by 489 days.

(21) Appl. No.: 13/503,542

(22) PCT Filed: Oct. 22, 2010

(86) PCT No.: PCT/EP2010/066007
§ 371 (c)(1),
(2), (4) Date: Nov. 2, 2012

(87) PCT Pub. No.: WO2011/048222
PCT Pub. Date: Apr. 28, 2011

(65) Prior Publication Data
US 2013/0052174 A1   Feb. 28, 2013

(30) Foreign Application Priority Data
Oct. 23, 2009 (GB) .................................. 0918615.6

(51) Int. Cl.
*A61K 35/12* (2015.01)
*C12N 5/0783* (2010.01)

(52) U.S. Cl.
CPC ...... *C12N 5/0637* (2013.01); *A61K 2035/122* (2013.01); *C12N 2501/23* (2013.01); *C12N 2502/1323* (2013.01); *C12N 2502/1382* (2013.01)

(58) Field of Classification Search
CPC ...... A61K 35/12; C12N 5/0783; C12N 5/078; A61P 17/06
USPC .................................................... 424/93.71
See application file for complete search history.

(56) References Cited

U.S. PATENT DOCUMENTS 7,048,922 B2 * 5/2006 Yang ............................. 424/93.7
2012/0064031 A1 * 3/2012 Buescher et al. ............ 424/85.2

FOREIGN PATENT DOCUMENTS

| EP | 1870452 | 12/2007 | |
|---|---|---|---|
| WO | WO 2005/094353 | 10/2005 | |
| WO | WO 2007039150 A2 * | 4/2007 | ......... A61K 39/0008 |

OTHER PUBLICATIONS

Tough, David et al. T Cell Stimulation in Vivo by LPS. J. Exp. Med. The Rockefeller University Press. vol. 185, No. 12, Jun. 16, 1997 2089-2094.*
Kang, Jung et al. Soluble Factors—Mediated Immunomodulatory Effects of Canine Adipose Tissue-Derived Mesenchymal Stem Cells. Stem Cells and Development 17:681-694 (2008) © Mary Ann Liebert, Inc.*
Bocelli-Tyndall, et al., "Human bone marrow mesenchymal stem cells and chondrocytes promote and/or suppress the in vitro proliferation of lymphocytes stimulated by interleukins 2, 7 and 15," Annals of the Rheumatic Diseas, vol. 68, Aug. 2009, pp. 1352-1359.
Di Nicola, et al., "Human bone marrow stromel cells suppress T-lymphocyte proliferation induced by celluar or nonspecific mitogenic stimuli," Blood, American Society of Hemotology, vol. 99, May 2002, pp. 3838-3843.
Guo et al., "Fetal BM-derived mesenchymal stem cells promote the expansion of human Th17 cells, but inhibit the production of Th1 cells," European Journal of Immunology, vol. 39, Oct. 2009, pp. 2840-2849.
Yang, et al., "Effect of human bone marrow mesenchymal stem cells on allogeneic regulatory T cells and its possible mechanism," Journal of Experimental Hemotology, vol. 16, Aug. 2007, pp. 785-789 (Abstract—XP002620769).
Najar, et al., "Mesenchymal stromal cells promote or suppress the proliferation of T lymphocytes from cord blood and peripheral blood: the importance of low cell ratio and role of interleukin-6," Cytotherapy, vol. 11, Sep. 2009, pp. 570-583.
Prevosto, et al., "Generation of CD4* or CD8* regulatory T cells upon mesenchymal stem cell-lymphocyte interaction," Haematologica—The Hematology Journal, vol. 92, Jul. 2007, pp. 881-888.
Yanez, et al., "Adipose Tissue-Derived Mesenchymal Stem Cells Having In Vivo Immunosuppressive Properties Applicable for the Control of the Graft-Versus-Host Disease," Stem Cells, vol. 24, Nov. 2006, pp. 2582-2591.
Raulf-Heimsoth, "T cell-primary culture from peripheral blood", Methods Mol Med, 2008, 138:17-30.
Schaldaferri et al., AGA Abstracts, 2009, Suppl 1., A-111.
Di Ianni et al., "Mesenchymal cells recruit and regulate T regulatory cells", Experimental Hematology, 2008, 36:309-318.

* cited by examiner

*Primary Examiner* — Scott Long
*Assistant Examiner* — Nghi V Nguyen
(74) *Attorney, Agent, or Firm* — Klauber & Jackson LLC (57) ABSTRACT

A method for the preparation and/or generation of immunomodulatory cells which comprises contacting a mesenchymal stem cell (MSC) and/or fibroblast cell population with peripheral blood leukocytes for between about 2 hours and about 25 days is described herein.

7 Claims, 3 Drawing Sheets

CELL POPULATIONS HAVING IMMUNOREGULATORY ACTIVITY, METHODS FOR THE PREPARATION AND USES THEREOF

CROSS REFERENCE TO RELATED APPLICATIONS

The present application is a National Stage Application claiming the priority of co-pending PCT Application No. PCT/EP2010/066007 filed Oct. 22, 2010, which in turn, claims priority from Great Britain application Serial No. 0918615.6 filed Oct. 23, 2009. Applicants claim the benefits of 35 U.S.C. § 120 as to the PCT application and priority under 35 U.S.C. § 119 as to the said Great Britain application, and the entire disclosures of both applications are incorporated herein by reference in their entireties.

FIELD OF THE INVENTION

The present invention relates to methods for providing immunomodulatory cells, and therapeutic uses of the cells for the immune modulation of mammals in need thereof.

BACKGROUND OF THE INVENTION

The immune system in higher vertebrates is the first line of defence against various antigens that can enter the vertebrate body, including micro-organisms such as bacteria, fungi and viruses that are the causative agents of a variety of diseases. Moreover, the immune system is also involved in a variety of other diseases or disorders, including autoimmune or immunopathologic diseases, immunodeficiency syndromes, atherosclerosis and various neoplastic diseases. Although methods are available for treating these diseases, many current therapies provide less than adequate results, and carry the risk of significant side effects. Among new emergent therapeutic strategies, those based on cell therapy appear to constitute a potentially useful tool for treating a great number of diseases. Thus, a great effort is currently being made by researchers in order to achieve said aim.

Autoimmune Diseases

Autoimmune diseases are caused when the body's immune system, which is meant to defend the body against bacteria, viruses, and any other foreign product, malfunctions and produces a pathological response against healthy tissue, cells and organs.

T cells and macrophages provide beneficial protection, but can also produce harmful or deadly immunological responses. Autoimmune diseases can be organ specific or systemic and are provoked by different pathogenic mechanisms. Systemic autoimmune diseases involve polyclonal B cell activation and abnormalities of immunoregulatory T cells, T cell receptors and MHC genes. Examples of organ specific autoimmune diseases are diabetes, hyperthyroidism, autoimmune adrenal insufficiency, pure red cell anemia, multiple sclerosis and rheumatic carditis. Representative systemic autoimmune diseases include systemic lupus erythematosus, chronic inflammation, Sjogren's syndrome, polymyositis, dermatomyositis and scleroderina.

Current treatment of autoimmune diseases involves administering immunosuppressive agents such as cortisone, aspirin derivatives, hydroxychloroquine, methotrexate, azathioprine and cyclophosphamide or combinations thereof. The dilemma faced when administering immunosuppressive agents, however, is that the more effectively the autoimmune disease is treated, the more defenseless the patient is left to attack from infections, and the more susceptible the patient is to developing tumors. Thus, there is a great need for new therapies for the treatment of autoimmune diseases.

Inflammatory Disorders

Inflammation is a process by which the body's white blood cells and secreted factors protect our bodies from infection by foreign substances, such as bacteria and viruses, and is a common process in autoimmune diseases. Secreted factors known as cytokines and prostaglandins control this process, and are released in an ordered and self-limiting cascade into the blood or affected tissues. In general, the current treatments for chronic inflammatory disorders have a very limited efficacy, and many of them have a high incidence of side effects or cannot completely prevent disease progression So far, no treatment is ideal, and there is no cure for these type of pathologies. Thus, there is a great need for new therapies for the treatment of inflammatory disorders.

Inhibition of T-Cell Responses

All immune responses are controlled by T cells. Self-reactive cells with the potential to elicit autoimmune responses comprise a part of the normal T cell repertoire, but in the healthy state, their activation is prevented by suppressor cells. Although T suppressor cells were originally described in the 1970s, significant progress in characterizing T-cell subsets has been made only recently, when they have been renamed as regulatory T cells.

There are different CD4+, CD8+, natural killer cell, and gamma and delta T cell subsets with regulatory (suppressor) activity. Two major types of T-reg cells have been characterized in the CD4+ population, i.e., the naturally-occurring, thymus-generated T-reg cells, and the peripherally-induced, IL-10 or TGF-beta secreting T-reg cells (Trl cells). The CD4+CD25+, Foxp3 -expressing, naturally-occurring T-reg cells generated in thymus, migrate and are maintained in the periphery.

Cell Therapy

Regulatory T-cell administration has long been identified as having significant potential in addressing key causes of immune and inflammatory disorders. However, there are currently no preparation protocols suitable for use in the large scale manufacture of regulatory T-cells and accordingly clinical development of regulatory T-cell therapies has been severely limited.

Mesenchymal stem cells (MSCs) are multipotent adult stem cells capable of differentiation into mesenchymal-type cells (adipocytes, osteoblasts and chondrocytes), but also myocytes, neurons, endothelial cells, astrocytes and epithelial cells. Although first reported in the normal adult bone marrow (BM-MSC), MSCs can also be obtained from other sources, such as umbilical cord blood, peripheral blood and adipose tissue. It has been observed that the in-vivo administration of mesenchymal stem cells appears to be associated with an upregulation of regulatory T-cells. Moreover, methods for the in-vitro preparation of T-reg cells (for their use in the treatment of immune and inflammatory disorders) are known in the art. For example PCT Patent Application WO2007039150 provides a method for the preparation of said cells by contacting mesenchymal stem cells with peripheral blood leukocytes. However, at present there still remains a long felt need for a means for the preparation of regulatory T-cells in a manner suitable for use in clinical as opposed to research applications.

SUMMARY OF THE INVENTION

In one aspect, the invention relates to the preparation and/or generation of immunomodulatory cells suitable for use in the treatment of a recipient subject. Said cells as well as kits comprising thereof constitute further aspects of the invention. In another aspect, the invention relates to the use of said immunomodulatory cells as a medicament, in the preparation of a medicament, for inducing transplantation tolerance, for treating autoimmune diseases, or for treating an inflammatory disease.

In another aspect, the invention relates to the use of said immunomodulatory cells in the preparation of a medicament, such as a medicament for the prevention, treatment or amelioration of one or more symptoms of disorders in which modulation of a subject's immune system is beneficial, e.g. , a medicament for inducing transplantation tolerance, or a medicament for treating autoimmune diseases, or a medicament for treating an inflammatory disease, or a medicament for treating allergies, for example, but not limited to, hypersensitivity Type IV reactions.

In another aspect, the invention relates to the use of said immunomodulatory cells, for preventing, treating, or ameliorating one or more symptoms associated with autoimmune diseases, inflammatory disorders, or immunologically mediated diseases including rejection of transplanted organs and tissues. In another aspect, the invention relates to a method of preventing, treating, or ameliorating one or more symptoms associated with autoimmune diseases, inflammatory disorders, or immunologically mediated diseases, in a subject suffering from any of said disorders or diseases, which comprises administering to said subject in need of such treatment a prophylactically or therapeutically effective amount of said immunomodulatory cells. The invention also relates to the use of such methods in combination therapy, in other words, immunomodulatory cells of the invention are co-administered with one or more agents, either simultaneously with the second or further agent, or separately, e g , sequentially.

In another aspect, the invention relates to a pharmaceutical composition comprising said immunomodulatory cells and a pharmaceutical carrier.

In another aspect, the invention relates to kits comprising said immunomodulatory cells.

DETAILED DESCRIPTION OF THE INVENTION

The present invention provides methods for the preparation and/or generation of immunomodulatory cells having immunomodulatory properties.

Definitions

In order to facilitate the understanding of the present description, the meaning of some terms and expressions in the context of the invention will be explained below. Further definitions will be included throughout the description as necessary.

The term "allogeneic" as used herein shall be taken to mean from different individuals of the same species. Two or more individuals are said to be allogeneic to one another when the genes at one or more loci are not identical.

The term "autologous" as used herein shall be taken to mean from the same individual.

The term "antigen presenting cells" (APC) refers to a cell population that displays surface foreign antigen complexed with major histocompatibility complex MHC. Although almost every cell in the body is capable of presenting antigens to T cells, the term "antigen presenting cells" (APC) is herein limited to those specialized cells that express surface MHC II (HLA DP, DQ, DR), and include both those cells in which this expression is induced (for example but not limited to B-cells and CD4 PHA blasts) and also those cells that are derived from the monocyte-macrophage lineage (for example, but not limited to, dendritic cells).

The term "autoimmune disease" refers to a condition in a subject characterized by cellular, tissue and/or organ injury caused by an immunological reaction of the subject to its own cells, tissues and/or organs. Illustrative, non-limiting examples of autoimmune diseases which can be treated with the immunomodulatory cells of the invention include alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, sarcoidosis, scleroderma, progressive systemic sclerosis, Sjogren's syndrome, Good pasture's syndrome, stiff-man syndrome, systemic lupus erythematosus, lupus erythematosus, takayasu arteritis, temporal arteritis/giant cell arteritis, ulcerative colitis, uveitis, vasculitides such as dermatitis herpetiformis vasculitis, vitiligo, Wegener's granulomatosis, Anti-Glomerular Basement Membrane Disease, Antiphospholipid Syndrome, Autoimmune Diseases of the Nervous System, Familial Mediterranean Fever, Lambert-Eaton Myasthenic Syndrome, Sympathetic Ophthalmia, Polyendocrinopathies, Psoriasis etc.

The term "inflammatory disease" refers to a condition in a subject characterized by inflammation, e.g. , chronic inflammation Illustrative, non-limiting examples of inflammatory disorders include, but are not limited to, Celiac Disease, rheumatoid arthritis (RA), Inflammatory Bowel Disease (IBD), asthma, encephalitis, chronic obstructive pulmonary disease (COPD), inflammatory osteolysis, allergic disorders, septic shock, pulmonary fibrosis (e.g. , idiopathic pulmonary fibrosis), inflammatory vacultides (e.g. , polyarteritis nodosa, Wegner's granulomatosis, Takayasu's arteritis, temporal arteritis, and lymphomatoid granulomatosus), post-traumatic vascular angioplasty (e.g., restenosis after angioplasty), undifferentiated spondyloarthropathy, undifferentiated arthropathy, arthritis, inflammatory osteolysis, chronic hepatitis, and chronic inflammation resulting from chronic viral or bacteria infections.

The term "Immune Mediated inflammatory Disease" shall be taken to mean any disease characterized by chronic or acute inflammation, resulting from, associated with or triggered by, a dysregulation of the normal immune response e.g. Crohn's disease, type 1 diabetes mellitus, rheumatoid arthritis, inflammatory bowel disease, psoriasis, psoriatic arthritis, ankylosing spondylitis, systemic lupus erythematosus, Hashimoto's disease, graft-versus-host disease, Sjogren's syndrome, pernicious anemia, Addison disease, scleroderma, Goodpasture's syndrome, ulcerative colitis, autoimmune hemolytic anemia, sterility, myasthenia gravis, multiple sclerosis, Basedow's disease, thrombopenia purpura, Guillain-Barré syndrome, allergy, asthma, atopic disease, arteriosclerosis, myocarditis, cardiomyopathy, glomerular nephritis, hypoplastic anemia, and rejection after organ transplantation.

The term "isolated" applied to a cell population refers to a cell population, isolated from the human or animal body, which is substantially free of one or more cell populations that are associated with said cell population in vivo or in vitro. The term "MHC" (major histocompatibility complex) refers to a subset of genes that encodes cell-surface antigen-presenting proteins In humans, these genes are referred to as human leukocyte antigen (HLA) genes. Herein, the abbreviations MHC or HLA are used interchangeably. The term "subject" refers to an animal, preferably a mammal including a non- primate (e g , a cow, pig, horse, cat, dog, rat, or mouse) and a primate (e g , a monkey, or a human). In a preferred embodiment, the subject is a human.

The term "immunomodulatory" refers to the inhibition or reduction of one or more biological activities of the immune system. The term "antigen specific immunomodulatory" refers to the inhibition or reduction of one or more biological activities of the immune system associated with a specific antigen or antigens, including both alloantigens and autoantigens. The term "immunomodulatory" shall be taken to comprise "antigen specific immunomodulatory".

The terms "immunomodulatory agent", "immunomodulatory cell population", "immunomodulatory cell" or "immunomodulatory cells" as used herein shall be taken to mean agents, cell(s) or populations thereof that inhibit or reduce one or more biological activities (for example, but not limited to, the proliferation, differentiation, priming, effector function, production of cytokines or expression of antigens) of one or more immune cells (for example, but not limited to, T cells). Immunomodulatory cells which may be generated according to methods of the invention include regulatory T cells such as T cells selected from CD4+ cells and CD25+ cells.

The term "T-cell" refers to cells of the immune system which are a subset of lymphocytes that express the T cell receptor (TCR). The term "regulatory T-cells" (also referred to herein as T-reg cells) refers to T cell subsets that actively suppress activation of the immune system and prevent pathological self-reactivity, i.e. an autoimmune disease. The term "regulatory T-cells" or "T-reg cells" shall be taken to include both naturally occurring t-cells (also known as CD4$^+$CD25$^+$FoxP3$^+$ T-reg cells) and adaptive T-cells (also known as Tr1 cells or Th3 cells) which do not express the FoxP3 molecule.

In a particularly preferred embodiment of the present method said immunomodulatory agents, cell(s) or populations thereof are regulatory T-cells, however in an alternative embodiment of the method they may be cells of other phenotypes that have been modified such that they are capable of performing the immunosuppressive functions of regulatory T-cells. For example, cells of other phenotypes may have previous to said modification lacked one or more of the following capabilities: suppression of a mixed lymphocyte reaction; suppression of a cytotoxic T cell response; inhibition of DC maturation; inhibition of T cell production of inflammatory cytokines.

As used herein, "negative" or "−" as used with respect to cell surface markers shall be taken to mean that mean that, in a cell population, less than 20%, 10%, preferably less than 9%, less than 8%, less than 7%, less than 6%, less than 5% less than, 4%, less than 3%, less than 2%, less than 1% or none of the cells express said marker. Expression of cell surface markers may be determined for example by means of flow cytometry for a specific cell surface marker using conventional methods and apparatus (for example a Beckman Coulter Epics XL FACS system used with commercially available antibodies and standard protocols known in the art).

As used herein the term mesenchymal stem cell (also referred to herein as "MSC") shall be taken to mean a multipotent cell type originally derived from the mesenchyme.

As used herein, the expression "significant expression" or its equivalent terms "positive" and "+" when used in regard to a cell surface marker shall be taken to mean that, in a cell population, more than 20%, preferably more than, 30%, more than 40%, more than 50%, more than 60% more than , 70%, more than 80%, more than 90% or all of the cells of the cells express said marker.

Expression of cell surface markers may be determined for example by means of flow cytometry for a specific cell surface marker using conventional methods and apparatus (for example a Beckman Coulter Epics XL FACS system used with commercially available antibodies and standard protocols known in the art) that show a signal for a specific cell surface marker in flow cytometry above the background signal using conventional methods and apparatus (for example, a Beckman Coulter Epics XL FACS system used with commercially available antibodies and standard protocols known in the art). The background signal is defined as the signal intensity given by a non-specific antibody of the same isotype as the specific antibody used to detect each surface marker in conventional FACS analysis. For a marker to be considered positive the specific signal observed is at least 20% stronger, preferably at least 30% stonger , at least 40% stronger, at least 50% stronger, at least 60% stronger, at least 70% stronger, at least 80% stronger, at least 90% stronger, at least 500% stronger, at least 1000% stronger, at least 5000% stronger, or at least 10000% stronger, than the background signal intensity using conventional methods and apparatus (for example a Beckman Coulter Epics XL FACS system used with commercially available antibodies and standard protocols known in the art).

Furthermore, commercially available and known monoclonal antibodies against said cell-surface markers (e.g. , cellular receptors and transmembrane proteins) can be used to identify relevant cells.

The term "connective tissue" refers to tissue derived from mesenchyme and includes several tissues which are characterized in that their cells are included within the extracellular matrix. Examples of connective tissues include but are not limited to, adipose and cartilaginous tissues.

The term "fibroblast" as used herein shall be taken to include fibroblast like synovial cells.

The term "gluten" shall be taken to mean a protein comprising of gliadin and glutenin components.

As used herein, the terms "treat", "treatment" and "treating" when used directly in reference to a patient or subject shall be taken to mean the amelioration of one or more symptoms associated with a disorder including, but not limited to, an inflammatory disorder, an autoimmune disease or an immunologically mediated disease including rejection of transplanted organs and tissues, wherein said amelioration results from the administration of the immunomodulatory cells of the invention, or a pharmaceutical composition comprising thereof, to a subject in need of said treatment.

The term "combination therapy" refers to the use of the immunomodulatory cells of the present invention or pharmaceutical compositions comprising thereof together with other active agents or treatment modalities, in the manner of the present invention for the amelioration of one or more symptoms associated with a disorder including, but not limited to, an inflammatory disorder, an autoimmune disease or an immunologically mediated disease including rejection of transplanted organs and tissues. These other agents or treatments may include known drugs and therapies for the treatment of such disorders such as but not limited to corticosteroids and non-steroidal anti-inflammatory compounds.

The immunomodulatory cells of the invention, or pharmaceutical compositions thereof, may also be combined with corticosteroids, non-steroidal anti-inflammatory compounds, or other agents useful in treating inflammation. The combined use of the agents of the present invention with these other therapies or treatment modalities may be concurrent, or given sequentially, that is, the two treatments may be divided up such that said immunomodulatory cells or a pharmaceutical composition comprising thereof may be given prior to or after the other therapy or treatment modality. The attending physician may decide on the appropriate sequence of administering the immunomodulatory cells, or a pharmaceutical composition comprising thereof, in combination with other agents, therapies or treatment modalities.

DETAILED DESCRIPTION

In one aspect, the present invention relates to methods for the preparation and/or generation of immunomodulatory cells that suppress activation of the immune system and prevent pathological self-reactivity, i e an autoimmune disease. In one embodiment said immunomodulatory cells are regulatory T-cells, in a particularly preferred embodiment said immunomodulatory cells are Foxp3+CD4+CD25+ T-reg and/or IL-10/TGFb-producing regulatory Tr1 cells. The immunomodulatory cells prepared and/or generated according to the method of the present invention constitute a further aspect of the instant invention.

Said method comprises contacting or culturing a MSC and/or fibroblast cell population with peripheral blood leukocytes. Said contact or culture period is preferably between about 2 hours and about 25 days, is more preferably between about 10 and about 18 days more preferably between about 4 and 16 days. An example period is between around 14 and 16 days. In a further embodiment said culture or contact is carried out for at least 4, at least 10, at least 12, at least 14, or at least 15 days. This co-culturing will result in the production of immunomodulatory cells, which can be used for treatment of a subject.

The present invention also provides a method comprises contacting or culturing a MSC and/or fibroblast cell population with peripheral blood leukocytes in the presence of at least one agent selected from the group consisting of LPS, IL-4, IL-2 and GM-CSF.

Thus, in said method for preparing and/or generating immunoregulatory cells of the invention, a MSC and/or fibroblast cell population is cultured in vitro with peripheral blood leukocytes in the presence of at least one agent selected from the group consisting of LPS, IL-4, IL-2 and GM-CSF. The culture period is preferably between about 2 hours and about 25 days, is more preferably between about 10 and about 18 days more preferably between about 4 and 16 days. An example period is between around 14 and 16 days. In a further embodiment said culture or contact is carried out for at least 4, at least 10, at least 12, at least 14, or at least 15 days. This co-culturing will result in the production of immunomodulatory cells, which can be used for treatment of a subject.

MSC and/or Fibroblast Population

The term MSC and/or fibroblast cell population shall be used to describe any of a plurality of cells comprising essentially of mesenchymal stem cells; a plurality of cells comprising essentially of fibroblasts; a plurality of cells comprising essentially of mesenchymal stem cells and fibroblasts. It is preferred that the ratio of number of cells in said MSC and/or fibroblast cell population to peripheral blood leukocytes is between 1:1 and 1:150 respectively. It is further preferred that the ratio of number of cells in said MSC and/or fibroblast cell population to peripheral blood leukocytes is between 1:30 and 1:5. Accordingly, in one embodiment this may be about 1 MSC to every 25 peripheral blood leukocytes, 1 MSC and 1 fibroblast to every 25 peripheral blood leukocytes or 1 MSC to every 10 peripheral blood leukocytes.

In one embodiment of the method the agent is LPS (gram negative bacterial endotoxin lipopolysacharide). It is preferred that the LPS concentration is between 0.01 and 100 µg/ml, it is further preferred that said concentration is between 1 and 50 µg/ml e.g. about 10 µg/ml.

In one embodiment of the method the agent is IL-2. It is preferred that the LPS concentration is between about 0.01 and 1000 IU/ml, it is further preferred that said concentration is up to about 500, up to about 600, up to about 700, up to about 800 or up to about 900 IU/ml.

In an alternative embodiment said agent is either of GM-CSF and IL-4. GM-CSF and IL-4 are both cytokines. It is preferred that the concentration thereof is between 1 and 2000 IU/ml, it is further preferred that said concentration is between 500 and 1000 IU/ml.

In a further embodiment of the method both the agents IL-4 and GM-CSF are used in the method of the invention. It is preferred that the ratio of the concentration of GM-CSF to the concentration of IL-4 is between 5:1 or 1:1 and that the concentrations of each of said agents is between 1 and 2000 IU/ml, it is further preferred that said concentration is between 500 and 1000 IU/ml. Accordingly, in one embodiment this may be about 1000 IU/ml GM-CSF to 500 IU/ml IL-4.

The method(s) of the invention are preferably performed in a temperature and carbon dioxide controlled environment, e.g. in an incubator. The method is preferably preformed at about mammalian body temperature, accounting for regional variations, e.g. 37 degrees centigrade. It is also preferred that the method of the invention is carried out in an environment where carbon dioxide concentration is between 0% and 10% and more preferably between 1% and 5%.

MSC and/or fibroblast cell populations and peripheral blood leukocytes suitable for use in said method, and methods for the preparation thereof are as according to those described previously for use in other methods of the present invention.

In methods of the invention preferably a MSC cell population (particularly one of human origin) is contacted with PBLs.

Fibroblasts

The fibroblasts as used in the method of the present invention are mesenchyme derived connective tissue that are associated with the synthesis and maintenance of extra cellular matrix and shall be taken to include fibroblast like synovial cells. The fibroblasts can be obtained from any suitable animal, most preferably human.

MSC

The MSC used in the method of the present invention are preferably derived from connective tissue. In a preferred embodiment said MSC are derived from adipose tissue and in a further preferred embodiment from the stromal fraction of the adipose tissue. In an alternative embodiment, said MSC are obtained from chondrocytes of the hyaline cartilage. In a further embodiment, said MSC are obtained from skin. In another embodiment, said MSC are obtained from bone marrow.

The MSC can be obtained from any suitable source of connective tissue from any suitable animal, most preferably humans. It is preferred that said cells are obtained from non-pathological mammalian sources, preferably post-natal (e.g., rodent; primate). In a preferred embodiment, the MSC are obtained from a source of connective tissue, such as, but not limited to, the stromal fraction of adipose tissue, hyaline cartilage, bone marrow or skin. Most preferably said MSC of the method are obtained from non-pathological, post-natal, human stromal adipose tissue.

With respect to the intended recipient of the immunomodulatory cells as prepared by the method of the present invention, the MSC and/or fibroblast cells used in said above described method may be of either allogeneic (donor) or autologous (subject) origin. In one embodiment of the method said MSC and/or fibroblast cells are of allogeneic origin.

The MSC and/or fibroblast cells used in the method of the present invention may be characterized in that (i) they do not express markers specific for APCs, (ii) they do not express IDO constitutively, (iii) they express IDO upon stimulation with IFN-gamma, and in the case of MSC (iv) they present the capacity to be differentiated into at least two cell lineages. However, the MSC and/or fibroblast cells used in the method of the present invention are preferably characterized in that (i) they do not express markers specific for APCs, (ii) they express IDO constitutively, or alternatively (iii) they express IDO upon stimulation with IFN-gamma, and in the case of MSC (iv) they present the capacity to be differentiated into at least two cell lineages MSC Phenotype Markers The MSC used in the method of the present invention are preferably negative for markers associated with APC phenotypes. Accordingly it is preferred that said MSC are negative for at least one, two, three, four or preferably all of the following markers CD 11b; CD 11c; CDI 14; CD45; HLAII. Furthermore, the MSC are preferably negative for at least one, two, or preferably all of the following cell surface markers CD31; CD34; CD 133.

In a particular embodiment, the MSC as used in the present method are preferably characterised in that they express (i.e. are positive for) at least one, two, three, four, of or preferably all of the following cell surface markers CD9, CD44, CD54, CD90 and CD 105. Preferably, the MSC are characterised in that they have significant expression levels of at least one, two, three, four, of and preferably all of said cell surface markers (CD9, CD44, CD54, CD90 and CD 105).

Optionally, the MSC may also be negative for the cell surface marker CD 106 (VCAM-1). Examples of MSC suitable for use in the method of the present invention are described in the art, for example in WO2007039150 which is hereby incorporated by reference in its entirety.

Expression of IDO

It is preferred that the MSC used in the method of the present invention express IDO (indoleamine 2,3-dioxygenase), either constitutively, or upon stimulation with IFN-gamma. Thus in one embodiment they express IDO constitutively. In another embodiment they express IDO upon stimulation with IFN-gamma. Furthermore, it is preferred that said cells do not express IDO upon stimulation with other pro-inflammatory mediators by themselves, such us interleukin-1 (IL-I) used at a concentration of up to 3 ng/ml, tumour necrosis factor-alpha (TNF- alpha) used at a concentration of up to 50 ng/ml, or the endotoxin LPS used at a concentration of up to 100 ng/ml. Stimulation with IFN-gamma for example at 3 ng/ml or higher can also induce expression of HLAII in the MSC to give a positive signal as defined herein for a cell surface marker. Said expression can be detected by those skilled in the art using any known technique that allows the detection of the expression of specific proteins. Preferably, said techniques are cell cytometry techniques.

Differentiation

The MSC suitable for use in the method of the present invention may present the capacity to proliferate and be differentiated into at least two, more preferably three, four, five, six, seven or more cell lineages Illustrative, non-limiting examples of cell lineages into which said MSC can be differentiated include osteocytes, adipocytes, chondrocytes, tenocytes, myocytes, cardiomyocytes, hematopoietic-supporting stromal cells, endothelial cells, neurons, astrocytes, and hepatocytes. MSC can proliferate and differentiate into cells of other lineages by conventional methods. Methods of identifying and subsequently isolating differentiated cells from their undifferentiated counterparts can be also carried out by methods well known in the art.

MSC Cell Culture

Said MSC are also capable of being expanded ex vivo. That is, after isolation, said MSC can be maintained and allowed to proliferate ex vivo in culture medium. Such medium is composed of, for example, Dulbecco's Modified Eagle's Medium (DMEM), with antibiotics (for example, 100 units/ml Penicillin and 100[mu]g/ml Streptomycin) or without antibiotics, and 2 mM glutamine, and supplemented with 2-20% fetal bovine serum (FBS). It is within the skill of one in the art to modify or modulate concentrations of media and/or media supplements as necessary for the cells used. Sera often contain cellular and non-cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), porcine serum, sheep serum, rabbit serum, rat serum (RS), etc. It is also within the scope of the invention that if said MSC are of human origin, the cell culture medium is supplemented with a human serum, preferably of autologous origin. It is understood that sera can be heat-inactivated at 55-65° C. if deemed necessary to inactivate components of the complement cascade. Modulation of serum concentrations, withdrawal of serum from the culture medium can also be used to promote survival of one or more desired cell types. Preferably, said MSC will benefit from FBS concentrations of about 2% to about 25%. In another embodiment, the MSC can be expanded in a culture medium of definite composition, in which the serum is replaced by a combination of serum albumin, serum transferrin, selenium, and recombinant proteins including but not limited to insulin, platelet-derived growth factor (PDGF), and basic fibroblast growth factor (bFGF) as known in the art.

Many cell culture media already contain amino acids, however some require supplementation prior to culturing of cells. Such amino acids include, but are not limited to, L-alanine, L- arginine, L-aspartic acid, L-asparagine, L cysteine, L-cystine, L-glutamic acid, L-glutamine, L-glycine, and the like.

Antimicrobial agents are also typically used in cell culture to mitigate bacterial, mycoplasmal, and fungal contamination. Typically, antibiotics or anti-mycotic compounds used are mixtures of penicillin/streptomycin, but can also include, but are not limited to amphotericin (Fungizone(R)), ampicilhn, gentamicin, bleomycin, hygromacin, kanamycin, mitomycin, etc Hormones can also be advantageously used in cell culture and include, but are not limited to, D-aldosterone, diethylstilbestrol (DES), dexamethasone, b-estradiol, hydrocortisone, insulin, prolactin, progesterone, somatostatin/human growth hormone (HGH), etc.

Expanded Cells

In one embodiment the MSC and/or fibroblast cells may have been expanded prior to use in the method of the present invention. Methods for cell expansion are known in the art.

Irradiated Cells

In one embodiment the MSC and/or fibroblast cells may have been irradiated prior to their use in the method of the present invention. Irradiation of cells reduces their proliferative capabilities and survival times.

The irradiation may be carried out using a suitable controlled source of ionizing radiation, such a gamma irradiator device. The irradiation conditions must be experimentally adjusted by a person skilled in the art to determine the required exposure time to impart a radiation dose that causes the long term growth arrest of the MSC and/or fibroblast cells. In one embodiment said radiation dose is within a range selected from the group consisting of 1-100 Gy; 5-85 Gy, 10-70 Gy, 12-60 Gy however it is particularly preferred that said radiation dose is within the range of 15-45 Gy.

IFN-Gamma Stimulated MSC

In one embodiment the MSC and/or fibroblast cells may be stimulated with interferon gamma prior to use in the method of the present invention. IFN-gamma treatment of MSC for the stimulation thereof is known in the art and may be carried out by a person skilled in the art.

Mitomycin C Treated MSC

In one embodiment the MSC and/or fibroblast cells may be treated with Mitomycin C prior to use in the method of the present invention. Mitomycin C treatment of MSC is known in the art and may be carried out by a person skilled in the art.

Furthermore, if desired, the MSC and/or fibroblast cells can be subjected to a plurality of the treatments selected from the group consisting of irradiation, IFN-gamma and Mitomycin C prior to use in the method of the present invention.

The maintenance conditions of said MSC can also contain cellular factors that allow cells to remain in an undifferentiated form. It is apparent to those skilled in the art that prior to differentiation, supplements that inhibit cell differentiation must be removed from the culture medium. It is also apparent that not all cells will require these factors. In fact, these factors may elicit unwanted effects, depending on the cell type.

Preparation of Peripheral Blood Leukocytes (PBLs)

With respect to the intended recipient of the immunomodulatory cells as prepared by the above described method of the present invention, the peripheral blood leukocytes used in said method may be of either autologous or allogeneic origin. However it is preferred that they are of autologous origin (i.e. that they were obtained from the subject who subsequently receives the immunomodulatory cells or any treatment, medicament or pharmaceutical composition thereof). Methods for the isolation of peripheral blood leukocytes from whole blood are known in the art and include the use of Ficoll-Hypaque and/or red blood cell lysis procedures or commercially available means such as the LeucoPREP™ cell separation device (Becton Dickinson & Co.) and HISTOPAQUE™ (Sigma Diagnostics) solution.

Method for the Preparation of Antigen Specific Immunomodulatory Cells

The invention also provides methods for the preparation and/or or generation of immunomodulatory cells specific for a chosen antigen or group of antigens (hereinafter also referred to as antigen specific immunomodulatory cells) and the use of these in the treatment of disease or disorders relating to that antigen or group of antigens. Examples of such antigens are those that play a role in autoimmune diseases, such as, for example, rheumatoid arthritis, Crohn's disease, hypersensitivity reaction Type IV, lupus, psoriasis and other autoimmune disorders known in the art and described elsewhere herein. In one embodiment said antigen specific immunomodulatory cells are regulatory T-cells, in a particularly preferred embodiment said antigen specific immunomodulatory cells are Foxp3+CD4+CD25+ T-reg and/or IL-10/TGFb-producing regulatory Tr1 cells. The antigen specific immunomodulatory cells specific for a chosen antigen or group of antigens prepared and/or generated according to said method of the present invention constitute a further aspect of the instant invention.

In one embodiment said method comprises contacting a MSC and/or fibroblast cell population with peripheral blood leukocytes and a chosen antigen or group of antigens. Said contact or culture period is preferably between about 2 hours and about 25 days, is more preferably between about 10 and about 18 days more preferably between about 4 and 16 days. An example period is between about 14 to 16 days. In a further embodiment said culture or contact is carried out for at least 4, at least 10, at least 12, at least 14, or at least 15 days. This co-culturing will result in the production of immunomodulatory cells, which can be used for treatment of a subject.

The present invention also provides a method which comprises contacting or culturing a MSC and/or fibroblast cell population with peripheral blood leukocytes and a chosen antigen or group of antigens in the presence of at least one agent selected from the group consisting of LPS, IL-4, IL-2 and GM-CSF.

In another embodiment in the method for preparing and/or generating antigen specific immunomodulatory cells, a MSC and/or fibroblast cell population is cultured in vitro with peripheral blood leukocytes in the presence of at least one agent selected from the group consisting of LPS, IL-4, IL-2 and GM-CSF and a chosen antigen, group of antigens or cell types expressing and/or presenting said antigen or antigens.

In an alternative embodiment the method for the preparation and/or or generation of antigen specific immunoregulatory cells comprises (a) contacting peripheral blood leukocytes with a chosen antigen or group of antigens in the presence of at least one agent selected from the group consisting of LPS, IL-4, IL-2 and GM-CSF, (b) bringing said cell population into contact with a MSC and/or fibroblast cell population In one embodiment there is provided a method for the preparation and/or generation of immunomodulatory cells specific for a chosen antigen or group of antigens, which comprises
(a) contacting peripheral blood leukocytes with said chosen antigen or group of antigens in the presence of at least one agent selected from the group consisting of LPS, IL-4, IL-2 and GM-CSF,
(b) bringing said cell population into contact with a MSC and/or fibroblast cell population.

In step (a) of said method for preparing and/or generating antigen specific immunomodulatory cells peripheral blood leukocytes are cultured in vitro in the presence of a chosen antigen, group of antigens or cell types expressing and/or presenting said antigen or antigens. After a culture period of about 2, 4, 6, 12, 24, 48 or more hours, preferably between about 12 to about 24 hours, the cell population of the invention is further co-cultured, optionally after the removal of the antigen, group of antigens or cells carrying said antigen, with a MSC and/or fibroblast cell population. The culture period is preferably between about 2 hours and about 25 days, is more preferably between about 10 and about 18 days more preferably between about 4 and 16 days. An example period is between about 14 to 16 days. In a further embodiment said culture is carried out for at least 4, at least 10, at least 12, at least 14, or at least 15 days. The culture period is preferably between about 2 hours and about 25 days, is more preferably between about 10 and about 18 days more preferably between about 4 and 16 days. In a further embodiment said culture or contact is carried out for at least 4, at least 10, at least 12, at least 14, or at least 15 days. This co-culturing will result in the production of immunomodulatory cells, which can be used for treatment of a subject. This co-culturing will result in the production of immunomodulatory cells specific for the chosen antigen, which can be used for treatment of a subject.

The MSC and/or fibroblast cell population of the invention as used in this method may be from the subject to whom the antigen specific immunomodulatory cells are subsequently administered (autologous) or from a donor (allogeneic). It is preferred that they are allogeneic.

Antigen(s)

The antigen used in said methods for the preparation and/or generation of antigen specific immunomodulatory cells may be a chosen antigen, group of antigens or cell types expressing and/or presenting said antigen or antigens. In one embodiment the antigen is selected from a group comprising of: a mixture of autoantigens derived from a patient suffering with autoimmunity, a peptide antigen, a nucleic acid, an altered peptide ligand, a recombinant protein or fragments thereof. In one embodiment said antigens are associated with arthritis (such as but not limited to collagen antigens). In an alternative embodiment said antigens are associated with Celiac Disease (alternatively referred to as coeliac disease, c(o)eliac sprue, non-tropical sprue, endemic sprue, gluten enteropathy or gluten-sensitive enteropathy, and gluten intolerance). Antigens associated with Celiac Disease are members of the gluten family including some forms of prolamins (such as but not limited to antigens of gliadins, hordeins, and/or secalins). In a further embodiment said antigens are associated with multiple sclerosis (such as but not limited to myelin antigens). Methods for the isolation, purification and preparation of such antigens are known to the person skilled in the art.

Immunomodulatory Cell Selection

In certain aspects the invention provides immunoregulatory cells suitable for administration to a recipient subject. It is therefore preferred that said immunoregulatory cells possess relative phenotypic homogeneity. Accordingly, in an optional step of the methods of the invention the immunomodulatory cells of the invention are selected form the heterogenous cell culture. The immunomodulatory cells and antigen specific immunomodulatory cells of the invention can be selected and isolated by conventional means known by a skilled person in the art. Examples of such technique include FACS and immunomagnetic cell sorting.

Cell Expansion

In one embodiment of the method the immunomodulatory cells of the invention can be expanded in number ex vivo using culture techniques known in the art. As an alternative treatment methodology, the immunomodulatory cells of invention may be administered directly in vivo without any cell expansion.

Use of Immunomodulatory Cells of the Invention

The immunomodulatory cells of the invention can be used for preventing, treating or ameliorating one or more symptoms associated with disorders in which modulation of a subject's immune system is beneficial, including, but not limited to, autoimmune diseases, inflammatory disorders, and immunologically mediated diseases including rejection of transplanted organs and tissues. Said use constitutes an additional aspect of the present invention.

Thus, in another aspect, the immunomodulatory cells of the invention are used as a medicament. In a particular embodiment, medicaments comprising of the immunomodulatory cells of the invention may be used for inducing transplantation tolerance (including relieving symptoms of rejection of transplanted organs and tissues), or for treating, and thereby alleviating, symptoms of autoimmune or inflammatory disorders, or immunologically mediated diseases including immune mediated inflammatory diseases, in a subject suffering from any of said disorders or diseases. Thus, the immunomodulatory cells of the invention can be used to therapeutically or prophylactically treat and thereby alleviate symptoms of autoimmune or inflammatory disorders in a subject suffering from any of said disorders or to alleviate symptoms of immunologically mediated diseases in a subject suffering from said diseases. The immunomodulatory cells of the invention are of use in the treatment of autoimmune disease, inflammatory disorder or immunological mediated disease. Illustrative, non-limiting examples of said diseases and disorders which can be treated are those previously listed under heading "Definitions". In a particular embodiment, said inflammatory disease is a chronic inflammatory disease, such as, e.g., Celiac Disease, Multiple Sclerosis, Psoriasis, IBD or RA. In another aspect, the present invention relates to the use of the immunomodulatory cells of the invention for the preparation of a medicament for preventing, treating or ameliorating one or more symptoms associated with disorders in which modulation of a subject's immune system is beneficial, including, but not limited to, autoimmune diseases, inflammatory disorders, and immunologically mediated diseases including rejection of transplanted organs and tissues. Thus, the invention further refers to the use of the immunomodulatory cells of the invention for the preparation of a medicament for suppressing the immune response, or for inducing transplantation tolerance, or for treating autoimmune diseases, or for treating inflammatory disorders. Examples of said autoimmune diseases and inflammatory diseases have been previously mentioned. In a particular embodiment, disease is an inflammatory disease, such as a chronic inflammatory disease, e g, Celiac Disease, Multiple Sclerosis, Psoriasis, IBD or RA.

Use of Antigen Specific Immunomodulatory Cells

The invention also provides the use of the antigen specific immunomodulatory cells, prepared and/or generated according to the methods of the invention in the treatment of diseases and disorders related to said chosen antigen or groups of antigens by administration of said antigen specific immunomodulatory cells to a subject, most preferably the subject from which the peripheral blood leukocytes were obtained.

Thus, in another aspect, said antigen specific immunomodulatory cells are used as a medicament. In a particular embodiment, medicaments comprising of the antigen specific immunomodulatory cells as described herein may be used for the treatment of diseases and disorders related to said chosen antigen or groups of antigens. Thus, the antigen specific immunomodulatory cells can be used to therapeutically or prophylactically treat and thereby alleviate symptoms of autoimmune or inflammatory disorders in a subject suffering from any of said disorders or to alleviate symptoms of immunologically mediated diseases in a subject suffering from said diseases. The antigen specific immunomodulatory cells of the present invention are of use in the treatment of autoimmune disease, inflammatory disorder or immunological mediated disease. Illustrative, non-limiting examples of said diseases and disorders which can be treated are those previously listed under heading "Definitions". In a particular embodiment, said inflammatory disease is a chronic inflammatory disease, such as, e.g., Celiac Disease, Multiple Sclerosis, Psoriasis, IBD or RA. In another aspect, the present invention relates to the use of the antigen specific immunomodulatory cells of the invention for the preparation of a medicament for preventing, treating or ameliorating one or more symptoms associated with disorders in which modulation of a subject's immune system is beneficial, including, but not limited to, autoimmune diseases, inflammatory disorders, and immunologically mediated diseases including rejection of transplanted organs and tissues. Thus, the invention further refers to the use of the antigen specific immunomodulatory cells as described herein for the preparation of a medicament for suppressing the immune response associated with said antigen(s). Examples of said autoimmune diseases and inflammatory diseases have been previously mentioned In a particular embodiment, disease is an inflammatory disease, such as a chronic inflammatory disease, e g, Celiac Disease, Multiple Sclerosis, Psoriasis, IBD or RA.

The invention also provides a method of treatment or prophylaxis of diseases and disorders related to a chosen antigen or group of antigens which comprises administering to a subject in need thereof immunoregulatory cells produced according to methods of the invention. Suitably the immunoregulatory cells were prepared and/or generated by means of the PBLs obtained from the subject.

As used herein, the term "immunomodulatory cells of the invention" shall be taken to mean all immunomodulatory cells prepared and/or generated by the methods of the invention described herein including both expanded and non-expanded immunomodulatory cells and antigen specific immunomodulatory cells.

Pharmaceutical Compositions

The present invention provides pharmaceutical compositions for the treatment, prophylaxis, and amelioration of one or more symptoms associated with a disorder in which modulation of a subject's immune system is beneficial such as autoimmune diseases, inflammatory disorders, and immunologically mediated diseases including rejection of transplanted organs and tissues.

Thus, in another aspect, the invention relates to a pharmaceutical composition, hereinafter referred to as the pharmaceutical composition of the invention, comprising an immunomodulatory cell of the invention and a pharmaceutical carrier. Combinations of two or more of said type of cells are included within the scope of the pharmaceutical compositions provided by the instant invention.

The pharmaceutical composition of the invention comprises a prophylactically or therapeutically effective amount of one or more prophylactic or therapeutic agents (i.e., immunomodulatory cells of the invention), and a pharmaceutical carrier. Suitable pharmaceutical carriers are known in the art and are preferably those approved by a regulatory agency of the US Federal or a state government or listed in the U.S. Pharmacopeia, or European Pharmacopeia, or other generally recognized pharmacopeia for use in animals, and more particularly in humans. The term "carrier" refers to a diluent, adjuvant, excipient, or vehicle with which the therapeutic agent is administered. The composition, if desired, can also contain minor amounts of pH buffering agents. Examples of suitable pharmaceutical carriers are described in "Remington's Pharmaceutical Sciences" by E W Martin. Such compositions will contain a prophylactically or therapeutically effective amount of a prophylactic or therapeutic agent preferably in purified form, together with a suitable amount of carrier so as to provide the form for proper administration to the subject. The formulation should suit the mode of administration. In a preferred embodiment, the pharmaceutical compositions are sterile and in suitable form for administration to a subject, preferably an animal subject, more preferably a mammalian subject, and most preferably a human subject.

The pharmaceutical composition of the invention may be in a variety of forms. These include, for example, solid, semi-solid, and liquid dosage forms, such as lyophilized preparations, liquids solutions or suspensions, injectable and infusible solutions, etc. The preferred form depends on the intended mode of administration and therapeutic application.

The administration of the immunomodulatory cell population of the invention, or the pharmaceutical composition comprising same, to the subject in need thereof can be carried out by conventional means. In a particular embodiment, said cell population is administered to the subject by a method which involves transferring the cells to the desired tissue, either in vitro (e g, as a graft prior to implantation or engrafting) or in vivo, to the animal tissue directly. The cells can be transferred to the desired tissue by any appropriate method, which generally will vary according to the tissue type. For example, cells can be transferred to a graft by bathing the graft (or infusing it) with culture medium containing the cells. Alternatively, the cells can be seeded onto the desired site within the tissue to establish a population. Cells can be transferred to sites in vivo using devices such as catheters, trocars, cannulae, stents (which can be seeded with the cells), etc.

The cell populations and pharmaceutical compositions of the invention can be used in a combination therapy. In a specific embodiment, the combination therapy is administered to a subject with an inflammatory disorder that is refractory to one or more anti-inflammatory agents. In another embodiment, the combination therapy is used in conjunction with other types of anti-inflammatory agents including, but not limited to, nonsteroidal anti-inflammatory drugs (NSAIDs), steroidal anti-inflammatory drugs, beta-agonists, anticholingeric agents, and methyl xanthines. Examples of NSAIDs include, but are not limited to, Ibuprofen, celecoxib, diclofenac, etodolac, fenoprofen, Indomethacin, ketorolac, oxaprozin, nabumentone, suhndac, tolmentin, rofecoxib, naproxen, ketoprofen, nabumetone, etc. Such NSAIDs function by inhibiting a cyclooxgenase enzyme (e g , COX-1 and/or COX-2). Examples of steroidal anti-inflammatory drugs include, but are not limited to, glucocorticoids, dexamethasone, cortisone, hydrocortisone, prednisone, prednisolone, triamcinolone, azulf[iota]dine, and eicosanoids such as thromboxanes, and leukotrienes. Monoclonal antibodies, such as Infliximab, can also be used.

In accordance with the above embodiment, the combination therapies of the invention can be used prior to, concurrently or subsequent to the administration of such anti-inflammatory agents. Further, such anti-inflammatory agents do not encompass agents characterized herein as lymphoid tissue inducers and/or immunomodulatory agents.

Kits

The present invention further relates to kits of use in the preparation and/or generation of immunomodulatory cells. Said kit comprises i) an MSC and/or fibroblast cell population, ii) at least one agent selected from the group consisting of LPS, IL-4, IL-2 and GM-CSF.

In one embodiment said agent is LPS (gram negative bacterial endotoxin lipopolysacharide). It is preferred that the LPS concentration is between 0.01 and 100 µg/ml, it is further preferred that said concentration is between 1 and 50 µg/ml e.g. about 10 µg/ml.

In one embodiment of the method the agent is IL-2. It is preferred that the LPS concentration is between about 0.01 and 1000 IU/ml, it is further preferred that said concentration is up to about 500, up to about 600, up to about 700, up to about 800 or up to about 900 IU/ml.

In an alternative embodiment said agent is either of GM-CSF and IL-4. It is preferred that the concentration thereof is between 1 and 2000 IU/ml, it is further preferred that said concentration is between 500 and 1000 IU/ml.

In a further embodiment both the agents IL-4 and GM-CSF are provided in said kit of the invention, either as a mixture or in separate containers. It is preferred that the ratio of the concentration of GM-CSF to the concentration of IL-4 is between 5:1 or 1:1 and that the concentrations of each of said agents is between 1 and 2000 IU/ml, it is further preferred that said concentration is between 500 and 1000 IU/ml. Accordingly, in one embodiment this may be about 1000 IU/ml GM-CSF to 500 IU/ml IL-4.

Preferably said MSC and/or fibroblast cell population is an allogeneic population. In one embodiment said cell population is comprised essentially of MSC. In a further embodiment said cell population is comprised essentially of fibroblasts. In a further alternative embodiment said cell population is comprised essentially of both fibroblasts and MSC. The MSC and/or fibroblast cell populations used in the kits of the present invention are preferably derived from human sources. In a preferred embodiment said MSC are derived from adipose tissue and in a further preferred embodiment from the stromal fraction of the adipose tissue. In an alternative embodiment, said MSC are obtained from chondrocytes of the hyaline cartilage. In a further embodiment, said MSC are obtained from skin. In another embodiment, said MSC are obtained from bone marrow.

In a further embodiment said kit further comprises iii) one or more antigens or cell types expressing and/or presenting said one or more antigens. In a further embodiment, said kits of the invention may comprise iv) instructions for use in the preparation and/or generation of immunomodulatory cells.

In a further embodiment the present invention provides kits of use in treating a subject with the immunomodulatory cells of the invention. Said kit comprises i) an immunomodulatory cell population prepared and/or generated according to the methods of the present invention or a medicament or a pharmaceutical composition thereof and ii) a device for administering said cells such as, but not limited to, syringes, injection devices, catheters, trocars, cannulae and stents. In a further embodiment, said kits of the invention may comprise iv) instructions for use in the treatment of a subject.

The features and advantages of the invention are more fully illustrated by the following non-limiting examples,

EXAMPLE 1

The aim of the following study was to identify optimal parameters for T-cell preparation using PBMC and stem cell co-cultures. Accordingly, the inventors investigated the effects of varying co-culture times, the addition of IL-2 to the co-cultures and also the use of fibroblast cells as an alternative to adipose derived stem cells.

Materials and Methods

Cell isolation and co-culture was carried out essentially as described in "Human adipose-derived mesenchymal stem cells reduce inflammatory and T cell responses and induce regulatory T cells in vitro in rheumatoid arthritis." Ann Rheum Dis. 2010 Jan;69(1):241-8. with minor modifications, and without the addition of antigens.

Human Stem Cell Isolation and Expansion

Human adipose-derived MSCs (hASCs) were obtained essentially as described in Zuk PA, Zhu M, Mizuno H, Huang J, Futrell J W, Katz A J, et al. Multilineage cells from human adipose tissue: implications for cell-based therapies. Tissue Eng 2001;7:211-28. Human adipose tissue was obtained by liposuction, under local anaesthesia and general sedation. A hollow blunt-tipped cannula was introduced into the subcutaneous space through a small incision (less than 0.5 cm in diameter). With gentle suction, the cannula was moved through the adipose tissue abdominal-wall compartment for mechanical disruption of the fatty tissue. A saline solution and the vasoconstrictor epinephrine were injected into the adipose tissue compartment to minimize blood loss. In this way, 80 to 100 ml of raw lipoaspirate were obtained from each patient to be treated.

The raw lipoaspirate was washed extensively with sterile phosphate-buffered saline (PBS; Gibco BRL, Paisley, Scotland, UK) to remove blood cells, saline and local anaesthetic. The extracellular matrix was digested with a solution of type II collagenase (0.075%; Gibco BRL) in balanced salt solution (5 mg/ml; Sigma, St. Louis, USA) for 30 minutes at 37° C. to release the cellular fraction. Then the collagenase was inactivated by addition of an equal volume of cell culture medium (Dulbecco's modified Eagle's medium (DMEM; Gibco BRL) that contained 10% fetal bovine serum (FBS; Gibco BRL). The suspension of cells was centrifuged at 250×g for 10 minutes. Cells were resuspended in 0.16 M NH$_4$Cl and allowed to stand for 5 minutes at room temperature (RT) for lysis of erythrocytes. The mixture was centrifuged at 250×g, and cells were resuspended in DMEM plus 10% FBS and 1% ampicillin/streptomycin mixture (Gibco BRL) and then they were filtered through a 40 μm mesh and were plated in tissue culture flasks at a concentration of 10-30×10$^3$ cells/cm$^2$. Cells were cultured for 24 hours at 37° C. in an atmosphere of 5% CO$_2$ in air. Then, the culture flasks were washed with PBS to remove non-adhering cells and cell fragments. The cells were maintained in culture in the same medium and under the same conditions until they reached approximately 80% confluence, with replacement of the culture medium every 3 to 4 days. Cells were then passaged with trypsin-EDTA (Gibco BRL) at a dilution of 1:3 which corresponds to a cell density of approximately about 5-6×10$^3$ cells/cm$^2$.

PBMC Preparation

PBMCs were isolated from buffy coats by density sedimentation using Ficollplaque Plus (GE Healthcare Biosciences AB, Uppsala). Cells recovered from the gradient interface were washed and stored until required.

Cell Cultures.

Long-term culture analysis:

PBLs were co-cultured with hASCs in a ratio of 1:25 in complete medium with the addition of 100 UI/ml of IL-2 in 96 well plates. As a control PBLs were cultured without hASCs. Cultures were maintained for up to 26 days, proliferation was evaluated by harvesting cells at regular intervals for FACS analysis.

IL-2 concentration analysis:

PBLs were co-cultured with hASCs in a ratio of 1:25 in complete medium with the addition of 25 UI/ml, 100 UI/ml, 500 UI/ml or 1000 UI/ml of IL-2 in 96 well plates. As a control PBLs were cultured without hASCs. After 15 days of culture, proliferation was evaluated by harvesting cells for FACS analysis.

Fibroblast culture analysis

PBMCs were co-cultured with fibroblasts instead of hASC in a ratio of 1:25 in complete medium with the addition of 100 UI/ml of IL-2 in 96 well plates. As a first control PBMCs were co-cultured without the addition of further cell types, and as a second control PBMCs were co-cultured with ASC instead of fibroblasts. After 15 days of culture, proliferation was evaluated by harvesting cells for FACS analysis.

FACS Analysis

Cells were stained with labelled antibodies against CD25 and CD4, as well as other relevant markers (e.g. FOXP3, results not shown) in order to detect the population of regulatory T cells. After washing, cells were fixed and acquired using a FACScalibur (BD Bioscience). CellQuest-pro software was used for acquisition and analysis. CALIBRITE beads (BD Bioscience) were used prior to each assay to calibrate the cytometer. Data were analyzed over gated lymphocytes (based on forward and side scatter properties).

Results

Long term culture analysis:

TABLE 1

CD4+CD25+ Cell Population Proliferation

|  |  | CD4+CD25+ | CD4+CD25+++ |
|---|---|---|---|
| Day 2 | PBL | 2.95 | 1.67 |
|  | ASC + PBL | 4.05 | 1.93 |

TABLE 1-continued

CD4+CD25+ Cell Population Proliferation

|  |  | CD4+CD25+ | CD4+CD25+++ |
|---|---|---|---|
| Day 4 | PBL | 6.76 | 1.86 |
|  | ASC + PBL | 9.76 | 3 |
| Day 10 | PBL | 23.58 | 2.97 |
|  | ASC + PBL | 27.95 | 7.15 |
| Day 16 | PBL | 25.17 | 3.55 |
|  | ASC + PBL | 41.63 | 21.28 |
| Day 18 | PBL | 20.82 | 1.89 |
|  | ASC + PBL | 38.94 | 4.57 |
| Day 23 | PBL | 24.48 | 2.24 |
|  | ASC + PBL | 34.69 | 3.9 |
| Day 26 | PBL | 32.26 |  |
|  | ASC + PBL | 25.54 |  |

Figure 1:
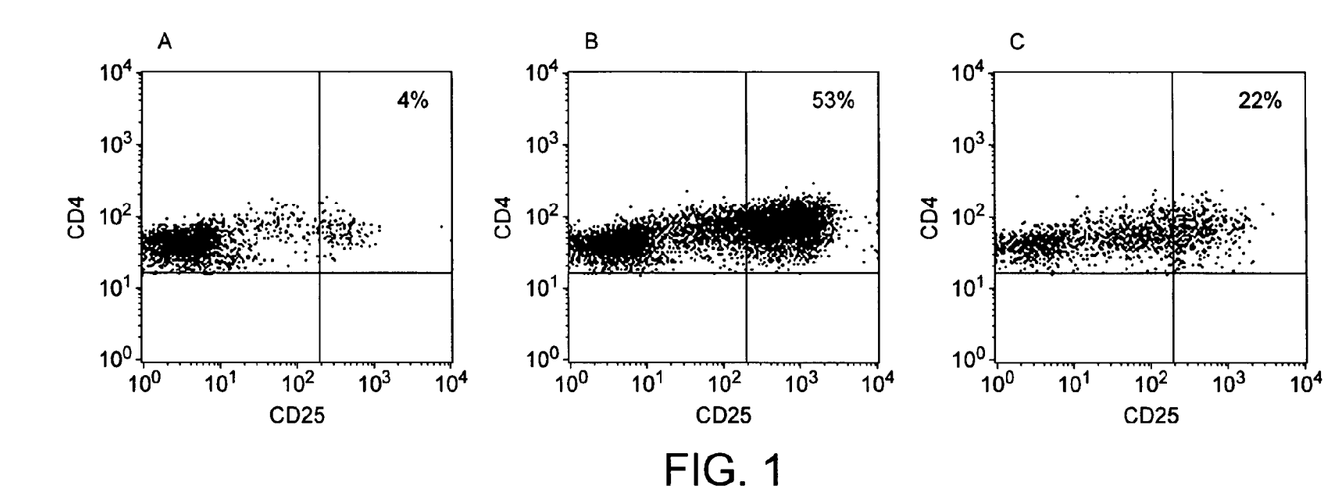
FIG. 1 provides a flow cytometry (FACS) dot plot profile of the cell population prepared according to Example 1 i).

FIG. 1 provides a flow cytometry (FACS) dot plot profile of the cell population prepared according to Example 1 i). Cells were isolated and stained at 4 (figure A), 15 (figure B) and 21 (figure C) days with fluorescent labeled antibodies directed against the membrane markers CD4 and CD25. The regulatory T-cell population makes up 4% of the analysed cell population at day 4, 53% at day 15 and 22% at day 21.

Figure 2:
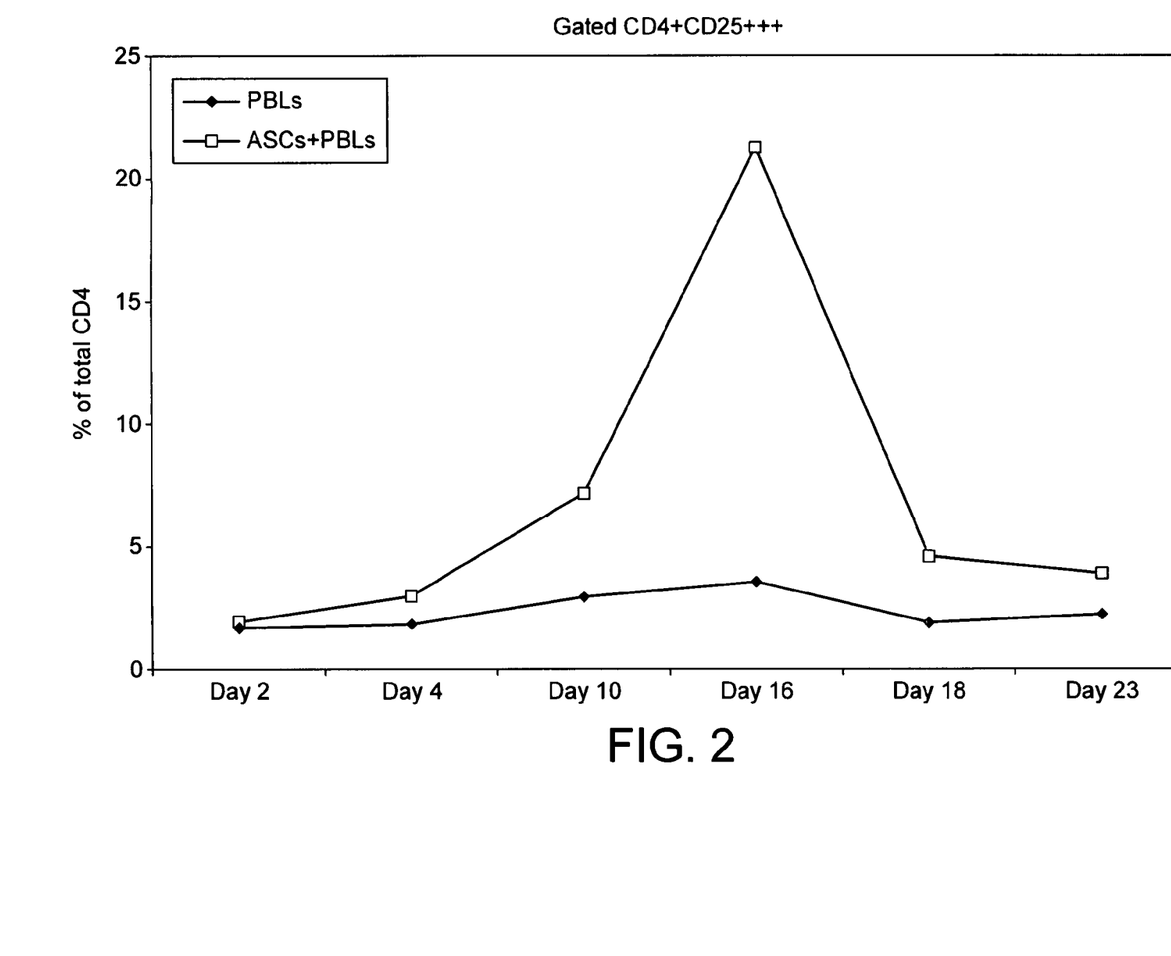
FIG. 2 provides a graphical representation of the cell population prepared according to Example 1 i).

FIG. 2 provides a graphical representation of the cell population prepared according to Example 1 i). Cells were isolated and stained at 2, 4, 10, 16, 18 and 23 days with fluorescent labeled antibodies directed against the membrane markers CD4 and CD25. The amount of CD25 positive cells in the co-culture is represented as a percentage of the total CD4 positive cell population.

It was concluded that the optimal time period for ASC PBL co-culture for preparation of regulatory T-cells was between about 4 and about 16 days, most preferably around 15 days.

Figure 3:
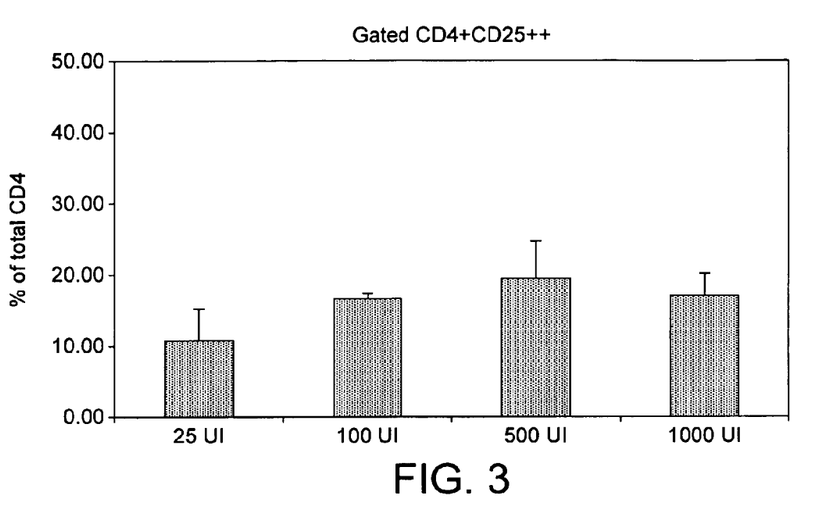
FIG. 3 provides a graphical representation of the various cell populations prepared according to Example 1 ii) using 25, 100, 500 and 1,000 IU/ml of IL-2.

IL-2 concentration analysis:

FIG. 3 provides a graphical representation of the various cell populations prepared according to Example 1 ii) using 25, 100, 500 and 1,000 UI/ml of IL-2. Cells were isolated and stained with fluorescent labeled antibodies directed against the membrane markers CD4 and CD25. The amount of CD25 positive cells in the co-culture is represented as a percentage of the total CD4 positive cell population. The optimal IL-2 concentration for preparation of regulatory T-cells was determined to be around 1000 Ul/ml.

Figure 4:
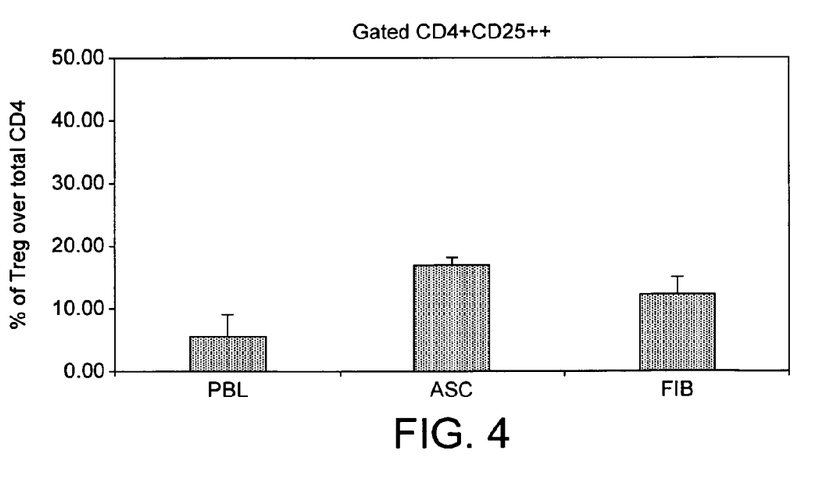
FIG. 4 provides a graphical representation of the various cell populations prepared according to Example 1 iii) using PBL culture alone ("PBL"), ASC+PBL co-culture ("ASC") or fibroblast+PBL co-culture ("FIB").

Fibroblast culture analysis:

FIG. 4 provides a graphical representation of the various cell populations prepared according to Example 1 iii) using PBL culture alone ("PBL"), ASC+PBL co-culture ("ASC") or Fibroblast-FPBL co-culture ("FIB"). Cells were isolated and stained with fluorescent labeled antibodies directed against the membrane markers CD4 and CD25. The amount of CD25 positive cells in the co-culture is represented as a percentage of the total CD4 positive cell population.

It was determined that ASC fibroblast co-culture may also be used in the preparation of regulatory T-cells, although the use of hASC is preferred.

Accordingly, while the invention has been described herein in reference to specific aspects, features and illustrative embodiments of the invention, it will be appreciated that the utility of the invention is not thus limited, but rather extends to and encompasses numerous other aspects, features, and embodiments. Accordingly, the claims hereafter set forth are intended to be correspondingly broadly construed, as including all such aspects, features, and embodiments, within their spirit and scope.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The invention claimed is:

1. A method for the preparation and/or generation of regulatory T cells which comprises contacting a mesenchymal stem cell (MSC) population derived from adipose tissue and which does not express indoleamine 2,3-dioxygenase (IDO) constitutively, with peripheral blood leukocytes for between 10 days and 18 days in the presence of IL-2.

2. The method according to claim 1 wherein the regulatory T cells are selected from CD4+ cells and CD25+ cells.

3. A method for the preparation and/or generation of regulatory T cells which comprises contacting a MSC population derived from adipose tissue and which does not express indoleamine 2,3-dioxygenase (IDO) constitutively, with peripheral blood leukocytes in the presence of IL-2 and at least one further agent selected from the group consisting of lipopolysaccharide (LPS), IL-4, and GM-CSF for between 10 days and 18 days.

4. The method according to claim 3 wherein said further agent is LPS.

5. The method according to claim 3 wherein said further agents are IL-4 and GM-CSF.

6. A method for the preparation and/or generation of regulatory T cells specific for a chosen antigen or group of antigens, which comprises contacting a MSC population derived from adipose tissue and which does not express indoleamine 2,3-dioxygenase (IDO) constitutively, with peripheral blood leukocytes and a chosen antigen or group of antigens in the presence of IL-2 and at least one further agent selected from the group consisting of lipopolysaccharide (LPS), IL-4, and GM-CSF for between 10 days and 18 days.

7. A method for the preparation and/or generation of regulatory T cells specific for a chosen antigen or group of antigens, which comprises
    (a) contacting peripheral blood leukocytes with said chosen antigen or group of antigens in the presence of IL-2 and at least one further agent selected from the group consisting of lipopolysaccharide (LPS), IL-4, and GM-CSF,
    (b) bringing said cell population into contact with a MSC population derived from adipose tissue and which does not express indoleamine 2,3-dioxygenase (IDO) constitutively for between 10 days and 18 days.

* * * * *